(12) United States Patent
Xia

(10) Patent No.: US 11,448,573 B2
(45) Date of Patent: Sep. 20, 2022

(54) EVAPORATION CLOSED CHAMBER FOR DETECTING HAZARDOUS SUBSTANCE

(71) Applicant: Dongguan City Simplewell Technology Co., Ltd, Guangdong (CN)

(72) Inventor: Keyu Xia, Guangdong (CN)

( * ) Notice: Subject to any disclaimer, the term of this patent is extended or adjusted under 35 U.S.C. 154(b) by 441 days.

(21) Appl. No.: 16/625,801

(22) PCT Filed: Aug. 2, 2018

(86) PCT No.: PCT/CN2018/098218
§ 371 (c)(1),
(2) Date: Dec. 23, 2019

(87) PCT Pub. No.: WO2020/000574
PCT Pub. Date: Jan. 2, 2020

(65) Prior Publication Data
US 2021/0333175 A1    Oct. 28, 2021

(30) Foreign Application Priority Data

Jun. 27, 2018    (CN) .......................... 201810682620.6

(51) Int. Cl.
*G01N 1/22*    (2006.01)
*G01N 1/40*    (2006.01)
*G01N 33/00*    (2006.01)

(52) U.S. Cl.
CPC .........  *G01N 1/2226* (2013.01); *G01N 1/4022* (2013.01); *G01N 33/0014* (2013.01); *G01N 2001/2241* (2013.01); *G01N 2033/0078* (2013.01)

(58) Field of Classification Search
None
See application file for complete search history.

(56) References Cited

FOREIGN PATENT DOCUMENTS

| CN | 106226483 | * | 12/2016 |
| CN | 108152451 | * | 6/2018 |

* cited by examiner

*Primary Examiner* — Daniel S Larkin
(74) *Attorney, Agent, or Firm* — Prakash Nama; Global IP Services, PLLC

(57) ABSTRACT

An evaporation closed chamber for detecting hazardous substance, having a closed chamber, an orifice plate, a pressure plate, a drive device and an elastic film, the orifice plate is mounted on any surface(s) of the closed chamber, the elastic film is arranged on the outer side of the orifice plate, the pressure plate is arranged on the outer side of the elastic film, and the drive device is in transmission connection with the pressure plate to drive the pressure plate to move forwards and backwards to press the elastic film against the orifice plate. The elastic film expands with the increase of internal temperature of the closed chamber and shrinks with the temperature decrease of the closed chamber such that the gas in the closed chamber can be timely compensated; the orifice plate prevents hazardous substance from leaving on the gas compensation device to influence test accuracy.

10 Claims, 4 Drawing Sheets

EVAPORATION CLOSED CHAMBER FOR DETECTING HAZARDOUS SUBSTANCE

BACKGROUND OF THE INVENTION

The present disclosure relates to the technical field of closed chambers, and more specifically, to an evaporation closed chamber for detecting a hazardous substance.

The existing automobile components, such as an oil tank, a tire, an automotive exterior trimming part, an automotive chassis and the like, may volatilize a hazardous substance, and when the concentration of the hazardous substance exceeds a certain range, the hazardous substance may cause damage to the human bodies. Therefore, it is necessary to collect and detect the hazardous substance of the automobile.

Currently, there are multiple systems for sampling and detecting the volatile hazardous substance in the industry. FIG. 3 shows a traditional evaporation closed chamber, which comprises a closed chamber 100, an internal compensation bag 200 and an external compensation bag 300, the internal compensation bag 200 is fixedly mounted in the closed chamber 100 through a bracket and is arranged at the upper portion of the interior of the closed chamber 100, and the external compensation bag 300 is communicated with the interior of the closed chamber 100 through a pipe. Before detection, a part or all of gas in the internal compensation bag 200 and the external compensation bag 300 is exhausted; and during detection, the internal compensation bag 200 and the external compensation bag 300 perform timely gas compensation on the interior of the closed chamber 100 along with reduction or increase of the gas in the closed chamber 100 to prevent polluting gas outside the closed chamber 100 from entering or exhausting the interior of the closed chamber 100 due to the gas pressure difference so as to improve the test accuracy. However, because a relatively large internal compensation bag 200 needs to be arranged, and the internal compensation bag 200 needs a relatively large bracket to be fixed, a certain amount of the hazardous substance is unavoidably left at the exterior of the internal compensation bag 200 and the bracket during the sampling and detecting so as to influence the test accuracy; meanwhile, during the sampling and detecting, the gas enters the external compensation bag 300, but the gas in the external compensation bag 300 is hard to be cleaned completely to cause that the hazardous substance is still left in the external compensation bag 300 and cannot be exhausted, thereby influencing the test accuracy.

BRIEF SUMMARY OF THE INVENTION

An objective of the present disclosure is to provide an evaporation closed chamber for detecting a hazardous substance, which can avoid influence of the external environment or other uncertain factors on a test result so as to be capable of effectively improving detection accuracy, in order to overcome the defects in the prior art.

To achieve the objective, the present disclosure provides an evaporation closed chamber for detecting the hazardous substance, which comprises a closed chamber and an intake device, the intake device is communicated with the interior of the closed chamber, the closed chamber is connected with an exhaust pipe, sampling openings are opened in the closed chamber, the closed chamber is provided with a gas compensation device for performing gas volume compensation on the interior of the closed chamber in a gas sampling process, the gas compensation device is arranged on one or more surfaces of the closed chamber, the gas compensation device comprises an orifice plate, a pressure plate, a drive device and an elastic film, the orifice plate is mounted on any surface or multiple surfaces of the closed chamber, the elastic film is arranged on the outer side face of the corresponding orifice plate, the pressure plate is arranged on the outer side face of the corresponding elastic film, and the drive device is in transmission connection with the corresponding pressure plate so as to drive the pressure plate to move forwards and backwards to tightly press the elastic film to be in contact with the orifice plate, the intake device comprises a first fan or pump, a filter and a valve, and the first fan or pump, the filter and the valve are communicated with the interior of the closed chamber.

Preferably, an insulating jacket covers the interior of the closed chamber, and the insulating jacket is provided with a temperature control system.

Preferably, a protective cover covers the outer side face of the gas compensation device, and the protective cover covers the outer side face of the pressure plate.

Preferably, a closed chamber door is arranged on the closed chamber, and a temperature and/or humidity control device is arranged at the interior/exterior of the closed chamber.

Preferably, a stirrer is arranged in the closed chamber.

Preferably, an anti-adsorption coating for preventing adsorption of hazardous substance is arranged on the inner wall of the closed chamber.

Preferably, an exhaust valve is arranged on the exhaust pipe.

Preferably, the closed chamber is connected with an internal purification device, the internal purification device comprises a purification loop, an air inlet valve, an air outlet valve, a purification filter and a second fan, and two ends of the purification loop are respectively connected with the closed chamber.

Preferably, an intake valve and an intake flow meter are arranged at the exterior of the closed chamber.

Preferably, the elastic film is a fluoride elastic film.

Compared with the prior art, beneficial effects of the present disclosure lie in:

The evaporation closed chamber for detecting the hazardous substance of the present disclosure has a simple structure and comprises the closed chamber and the gas compensation device for performing the gas volume compensation on the interior of the closed chamber in the gas sampling process, and the gas compensation device is arranged on one or more surfaces of the closed chamber, wherein the gas compensation device comprises the orifice plate, the pressure plate, the drive device and the elastic film, the orifice plate is mounted on any surface or multiple surfaces of the closed chamber, the elastic film is arranged on the outer side face of the corresponding orifice plate, the pressure plate is arranged on the outer side face of the corresponding elastic film, and the drive device is in transmission connection with the corresponding pressure plate so as to drive the pressure plate to move forwards and backwards to tightly press the elastic film to be in contact with the orifice plate; due to arrangement of the elastic film, the elastic film expands along with the increase of the temperature of the closed chamber and shrinks along with the reduction of the temperature of the closed chamber such that the gas in the closed chamber can be timely compensated; and arrangement of the orifice plate effectively prevents the hazardous substance from remaining on the gas compensation device to influence test accuracy; meanwhile, the whole structure is more simply arranged to effectively avoid influence of the external environment or other uncertain factors on a detection result so as to improve detection accuracy.

BRIEF DESCRIPTION OF THE DRAWINGS

To describe the technical solutions in the embodiments of the present disclosure or the prior art more clearly, the following briefly introduces the accompanying drawings required for describing the embodiments or the prior art. Apparently, the accompanying drawings in the following description show some embodiments in the present disclosure, and a person of ordinary skill in the art may still derive other drawings from these accompanying drawings without creative efforts.

DETAILED DESCRIPTION OF THE INVENTION

To make the objectives, technical solutions, and advantages of the embodiments of the present disclosure clearer, the following clearly and completely describes the technical solutions in the embodiments of the present disclosure with reference to the accompanying drawings in the embodiments of the present disclosure. Apparently, the described embodiments are some but not all of the embodiments of the present disclosure. All other embodiments obtained by a person of ordinary skill in the art based on the embodiments of the present disclosure without creative efforts shall fall within the protection scope of the present disclosure. All other embodiments obtained by a person of ordinary skill in the art based on the embodiments of the present disclosure without creative efforts shall fall within the protection scope of the present disclosure.

Embodiment 1

Figure 1:
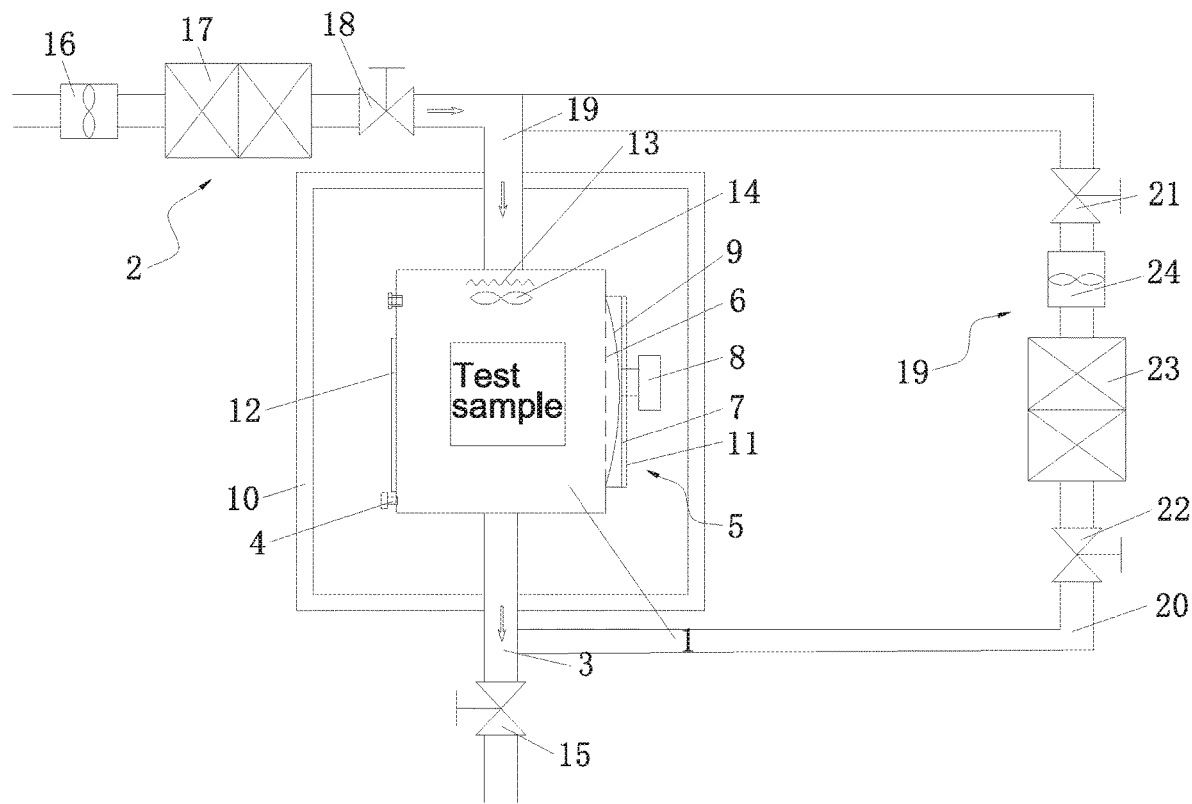
FIG. 1 is a schematic diagram of a whole structure of an evaporation closed chamber for detecting a hazardous substance, provided by the present disclosure.
Figure 2:
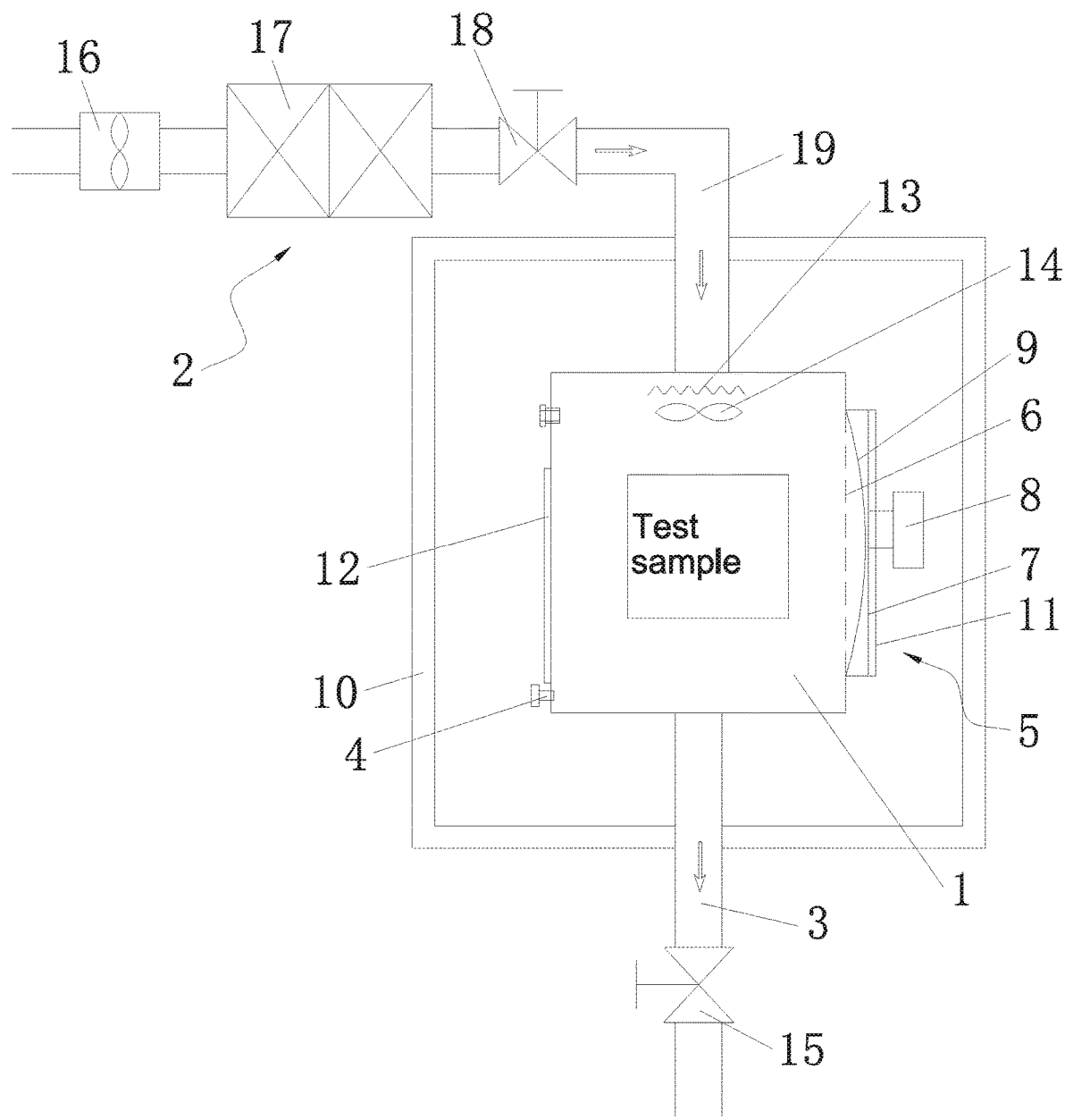
FIG. 2 is a schematic diagram of a partial structure of an evaporation closed chamber for detecting the hazardous substance, provided by the present disclosure.
Figure 3:
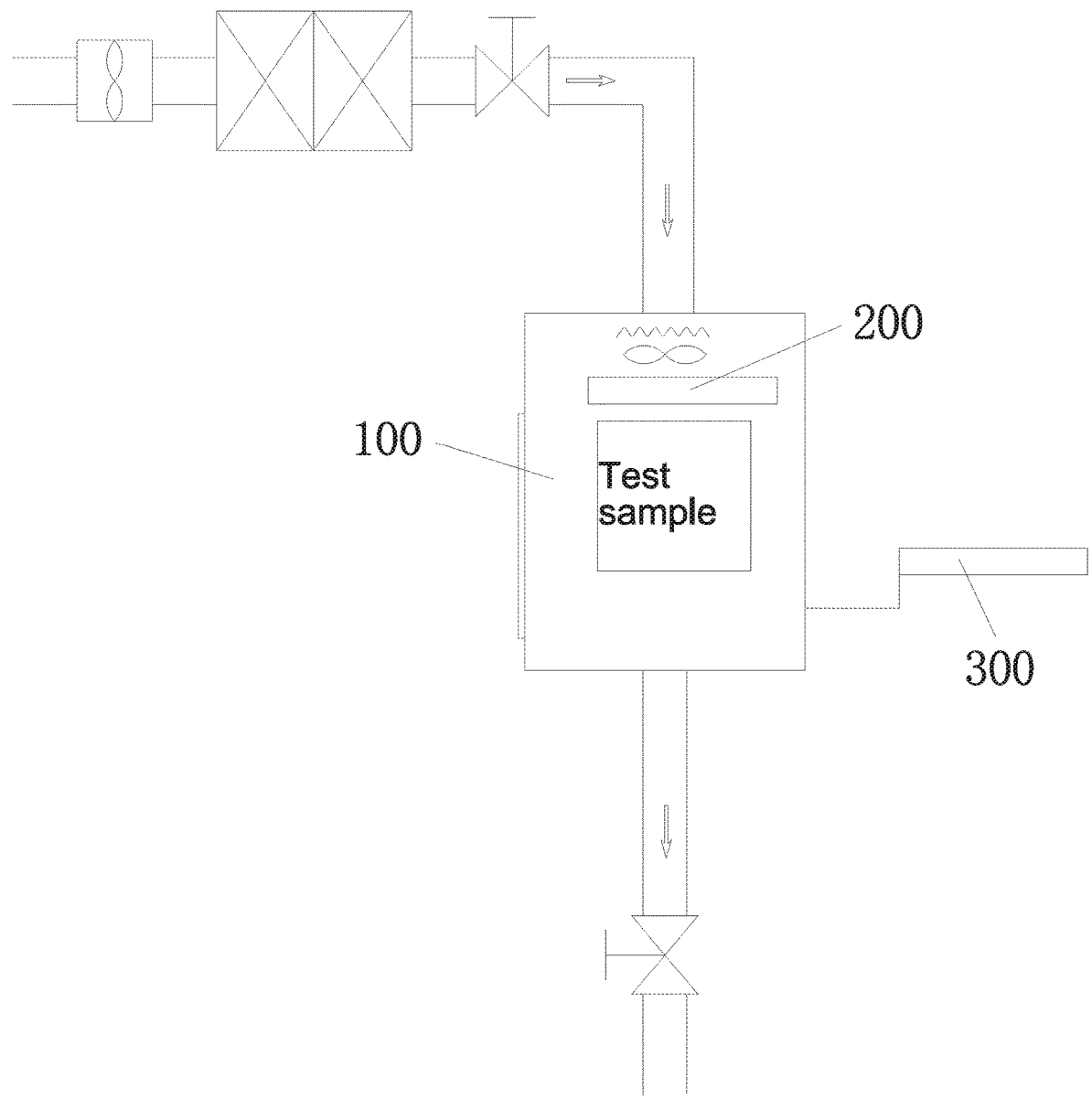
FIG. 3 is a schematic diagram of a whole structure of a traditional evaporation closed chamber provided by the present disclosure.

Referring to FIG. 1 and FIG. 2, Embodiment 1 of the present disclosure provides an evaporation closed chamber for detecting a hazardous substance, which comprises a closed chamber 1 and a gas compensation device 5 for performing gas volume compensation on the interior of the closed chamber 1 in a gas sampling process, and the gas compensation device 5 is arranged on one or more surfaces of the closed chamber 1, wherein the gas compensation device 5 comprises an orifice plate 6, a pressure plate 7, a drive device 8 and an elastic film 9, the orifice plate 6 is mounted on any surface or multiple surfaces of the closed chamber 1, the elastic film 9 is arranged on the outer side face of the corresponding orifice plate 6, the pressure plate 7 is arranged on the outer side face of the corresponding elastic film 9, and the drive device 8 is in transmission connection with the corresponding pressure plate 7 so as to drive the pressure plate 7 to move forwards and backwards to tightly press the elastic film 9 to be in contact with the orifice plate 6. The following describes the embodiment in detail with reference to the accompanying drawings.

As shown in FIG. 1 and FIG. 2, an intake device 2 is communicated with the interior of the closed chamber 1, the closed chamber 1 is connected with an exhaust pipe 3, sampling openings 4 are opened in the closed chamber 1, the closed chamber 1 is provided with the gas compensation device 5 for performing the gas volume compensation on the interior of the closed chamber 1 in the gas sampling process, the gas compensation device 5 is arranged on one or more surfaces of the closed chamber 1, the gas compensation device 5 comprises the orifice plate 6, the pressure plate 7, the drive device 8 and the elastic film 9, the orifice plate 6 is mounted on any surface or multiple surfaces of the closed chamber 1, the elastic film 9 is arranged on the outer side face of the corresponding orifice plate 6, the pressure plate 7 is arranged on the outer side face of the corresponding elastic film 9, the drive device 8 is in transmission connection with the corresponding pressure plate 7 so as to drive the pressure plate 7 to move forwards and backwards to tightly press the elastic film 9 to be in contact with the orifice plate 6, the elastic film 9 expands along with the increase of the internal temperature of the closed chamber 1 and shrinks along with the reduction of the temperature thereof such that the gas in the closed chamber 1 can be timely compensated, and due to arrangement of the orifice plate 6, the apertures of the orifice plate 6 are set to be large so as to be capable of allowing free flow of the gas in the closed chamber 1 and to effectively prevent the hazardous substance from remaining on the gas compensation device 5 to influence test accuracy; meanwhile the whole structure is more simply arranged to effectively avoid influence of the external environment or other uncertain factors on a detection result so as to improve detection accuracy.

Wherein the intake device 2 comprises a first fan or pump 16, a filter 17 and a valve 18, the first fan or pump 16, the filter 17 and the valve 18 are sequentially connected and are communicated with the interior of the closed chamber 1, and an exhaust valve 15 is arranged on the exhaust pipe 3. During preparation before a test starts, the first fan or pump 16 blows air to the interior of the closed chamber 1 to repeatedly replace air in the closed chamber 1, and after air replacement is completed, the valve 18 is closed to stop air intake and the exhaust valve 15 on the exhaust pipe 3 is closed to stop air exhaust, thereby completing the preparation. Before the test starts, the clean gas is aerated into the closed chamber 1, and original polluting gas in the closed chamber 1 is exhausted such that the gas in the closed chamber 1 is purified and exchanged, thereby providing a standard and stable test environment for detection, and effectively ensuring the detection accuracy.

Preferably, an insulating jacket 10 covers the exterior of the closed chamber 1, the insulating jacket 10 is provided with a temperature control system, and arrangement of the insulating jacket 10 effectively maintains the temperature of the closed chamber 1 and ensures the detection accuracy.

Preferably, a protective cover 11 covers the outer side face of the gas compensation device 5, and the protective cover 11 covers the outer side face of the pressure plate 7 so as to prevent the elastic film 9 from being damaged and effectively ensure the service life of the device.

In the embodiment, a closed chamber door 12 is arranged on the closed chamber 1, a temperature and/or humidity control device 13 is arranged at the interior/exterior of the closed chamber 1, and the temperature and/or humidity control device 13 is arranged to regulate the temperature and the humidity of the interior of the closed chamber 1 so as to provide a stable test environment for detection of the hazardous substance and improve the detection accuracy, wherein a stirrer 14 is arranged in the closed chamber 1, and the stirrer 14 is arranged to uniformly stir the gas in the closed chamber 1.

Preferably, an anti-adsorption coating for preventing adsorption of the hazardous substance is arranged on the inner wall of the closed chamber 1 to effectively prevent the hazardous substance from adsorbing on the inner wall of the closed chamber 1 to influence the test accuracy.

Preferably, the elastic film 9 is a fluoride elastic film, and specifically, the fluoride material may be polytetrafluoroethylene or other fluoride. Wherein a compensation bag made from the fluoride material can prevent volatile organic compounds from adsorbing on the outer wall of the compensation bag so as to improve the test accuracy.

Preferably, the closed chamber 1 is connected with an internal purification device 19, the internal purification device 19 comprises a purification loop 20, an air inlet valve 21, an air outlet valve 22, a purification filter 23 and a second fan 24, the air inlet valve 21, the air outlet valve 22, the purification filter 23 and the second fan 24 are sequentially connected through the purification loop 20, and two ends of the purification loop 20 are respectively connected with the closed chamber 1.

The evaporation closed chamber for detecting the hazardous substance comprises the following detection steps:

(1), opening the exhaust valve 15, starting a first fan or pump 16 and opening the valve 18 so that the external air passes through the filter 17 to be filtered and then enters the interior of the closed chamber 1 to replace polluting gas in the closed chamber 1 with cleaned gas; meanwhile, operating the stirrer 14 in the closed chamber 1 and operating the temperature and/or humidity control device 13;

(2), putting a test sample into the closed chamber 1, and starting the internal purification device 19 to clean the closed chamber 1;

(3), stopping the internal purification device 19, and closing the air inlet valve 21 and/or the air outlet valve 22;

(4), starting the drive device 8 to drive the pressure plate 7 to move and to tightly press the elastic film 9 and the orifice plate 6, controlling the internal temperature of the closed chamber 1 to be t1 and the internal volume of the closed chamber 1 to be V1;

(5), resetting the drive device 8, and increasing the internal temperature of the closed chamber 1 to be t2, so that the elastic film 9 expands and the internal volume of the closed chamber 1 is $V2=(273+T2)/(273+T1)*V1$;

(6), continuously increasing the internal temperature of the closed chamber 1 to be t3, so that the elastic film 9 continuously expands and the internal volume of the closed chamber 1 is $V3=(273+T3)/(273+T1)*V1$; and (7), after regulation is completed, maintaining the internal temperature of the closed chamber 1 to be at least t1 if the internal temperature of the closed chamber 1 drops after step (6), and controlling the internal temperature of the closed chamber 1 not to exceed t3 after step (6), such that the rest sample exhausts pollutant into the closed chamber 1 with the internal temperature of the closed chamber 1 maintained within a range from t1 to t3; and detecting the concentration of the pollutant in the closed chamber 1 from the sampling openings 4, and then obtaining an exhaust amount of the pollutant of the test sample in the test state.

Thereafter, the polluting gas in the closed chamber 1 is exhausted and is replaced with the clean gas before test so as to provide a clean and pollution-free test environment for the test to effectively improve the test accuracy; and in the sampling process, the elastic film 9 expands or shrinks along the change of the temperature to provide gas compensation for the interior of the closed chamber 1 so as to effectively prevent the external polluting gas from entering the closed chamber 1 due to the gas pressure difference and further improve the test accuracy.

Embodiment 2

Figure 4:
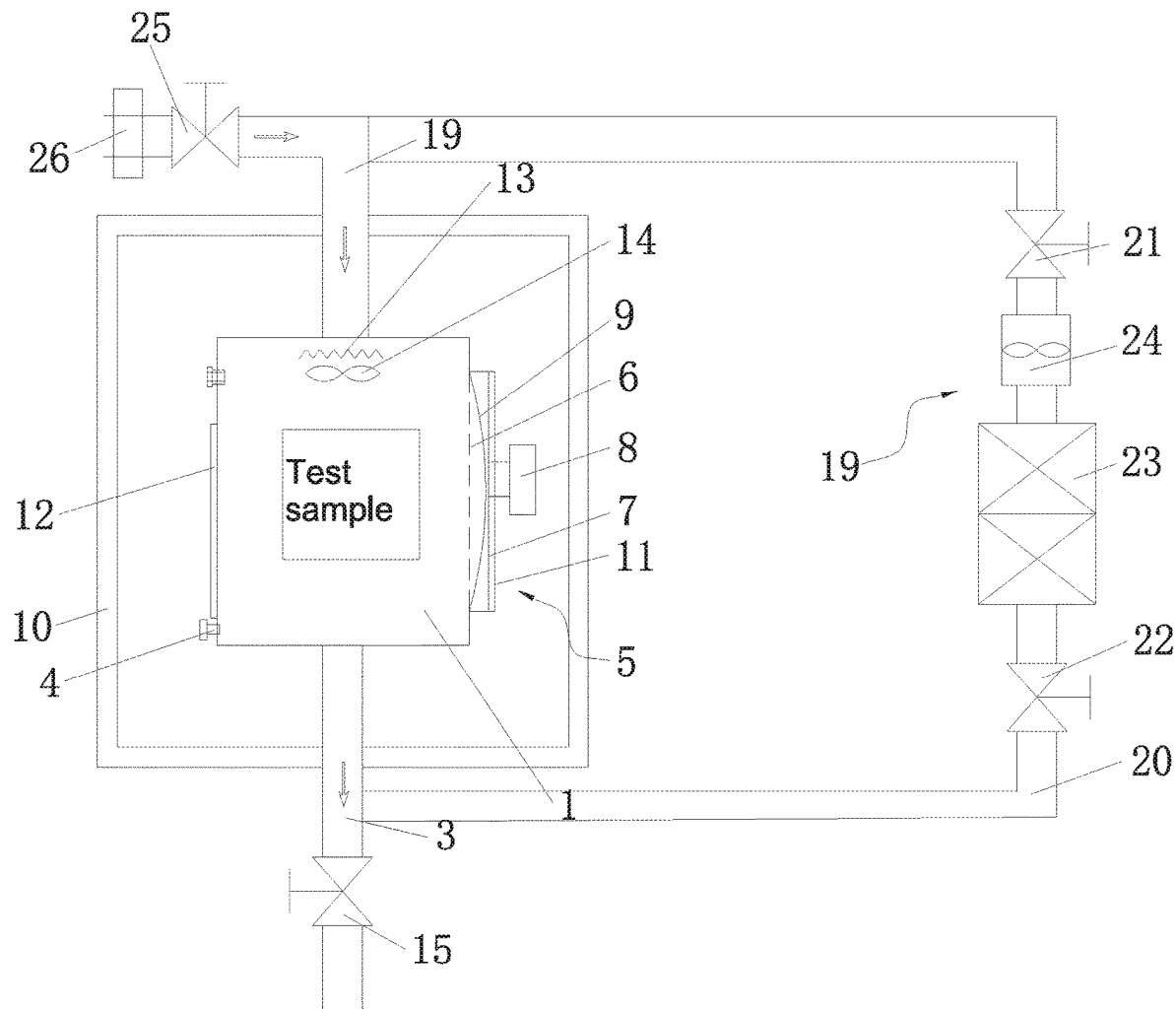
FIG. 4 is a schematic structural diagram of another evaporation closed chamber for detecting the hazardous substance, provided by the present disclosure.

As shown in FIG. 4, Embodiment 2 of the present disclosure provides another evaporation closed chamber for detecting the hazardous substance, an intake valve and an intake flow meter are arranged at the exterior of the closed chamber 1, the structure of the evaporation closed chamber for detecting the hazardous substance in Embodiment 2 of the present disclosure is mostly the same as the structure of the evaporation closed chamber for detecting the hazardous substance in Embodiment 1 of the present disclosure, and the same parts are not described again.

In the embodiment, the intake valve 25 and the intake flow meter 26 are arranged at the exterior of the closed chamber 1, the temperature of the closed chamber 1 is controlled to be t1, and at this time, the volume of the closed chamber 1 is V1; after the drive device 8 resets, the valves except the intake valve 25 are closed, the internal temperature of the closed chamber 1 is increased to be t2, and at this time, the volume of the closed chamber 1 is $V2=(273+T2)/(273+T1)*V1$; the intake flow meter 26 controls the flow rate of intake air to be (V2−V1), the elastic film 9 expands, the intake valve 25 is closed, and the internal temperature of the closed chamber 1 is increased to be t3; the internal temperature of the closed chamber 1 is controlled to change between t1 to t3, a test sample exhausts the pollutant into the closed chamber 1 in the temperature changing process, and the concentration of the pollutant in the closed chamber 1 is detected through the sampling openings 4 so as to obtain the exhaust amount of the pollutant of the test sample in the test state.

Thereafter, the polluting gas in the closed chamber 1 is exhausted and is replaced with the clean gas before test so as to provide a clean and pollution-free test environment for the test to effectively improve the test accuracy; and in the sampling process, the elastic film 9 expands or shrinks along the change of the temperature to provide gas compensation for the interior of the closed chamber 1 so as to effectively prevent the external polluting gas from entering the closed chamber 1 due to the gas pressure difference and further improve the test accuracy.

In conclusion, the evaporation closed chamber for detecting the hazardous substance of the present disclosure has a simple structure and comprises the closed chamber 1 and the gas compensation device 5 for performing the gas volume compensation on the interior of the closed chamber 1 in the gas sampling process, and the gas compensation device 5 is arranged on one or more surfaces of the closed chamber 1, wherein the gas compensation device 5 comprises the orifice plate 6, the pressure plate 7, the drive device 8 and the elastic film 9, the orifice plate 6 is mounted on any surface or multiple surfaces of the closed chamber 1, the elastic film 9 is arranged on the outer side face of the corresponding orifice plate 6, the pressure plate 7 is arranged on the outer side face of the corresponding elastic film 9, and the drive device 8 is in transmission connection with the corresponding pressure plate 7 so as to drive the pressure plate 7 to move forwards and backwards to tightly press the elastic film 9 to be in contact with the orifice plate 6; due to arrangement of the elastic film 9, the elastic film 9 expands along with the increase of the temperature of the closed chamber 1 and shrinks along with the reduction of the temperature of the closed chamber 1 such that the gas in the closed chamber 1 can be timely compensated; and arrangement of the orifice plate 6 effectively prevents the hazardous substance from remaining on the gas compensation device 5 to influence test accuracy; meanwhile, the whole structure is more simply arranged to effectively avoid influence of the external environment or other uncertain factors on a detection result so as to improve detection accuracy.

The above-mentioned embodiments are preferred embodiments of the present disclosure, but the implementation manner of the present disclosure is not limited to the embodiments. Any other changes, modifications, substitutions, combinations and simplifications without departing from the spirit essence and the principle of the present disclosure should be included within the protection scope of the present disclosure.

What is claimed is:

1. An evaporation closed chamber for detecting a hazardous substance, comprising a closed chamber (1) and an intake device (2), wherein the intake device (2) is communicated with the interior of the closed chamber (1), the closed chamber (1) is connected with an exhaust pipe (3), and sampling openings (4) are opened in the closed chamber (1); wherein the closed chamber (1) is provided with a gas compensation device (5) configured for performing gas volume compensation on the interior of the closed chamber (1) in a gas sampling process, the gas compensation device (5) is arranged on one or more surfaces of the closed chamber (1), the gas compensation device (5) comprises an orifice plate (6), a pressure plate (7), a drive device (8) and an elastic film (9), the orifice plate (6) is mounted on any surface or multiple surfaces of the closed chamber (1), the elastic film (9) is arranged on an outer side face of the corresponding orifice plate (6), the pressure plate (7) is arranged on an outer side face of the corresponding elastic film (9), and the drive device (8) is in transmission connection with the corresponding pressure plate (7) so as to drive the pressure plate (7) to move forwards and backwards to press the elastic film (9) to be in contact with the orifice plate (6), the intake device (2) comprises a first fan or pump (16), a filter (17) and a valve (18), and the first fan or pump (16), the filter (17) and the valve (18) are communicated with the interior of the closed chamber (1).

2. The evaporation closed chamber for detecting a hazardous substance according to claim 1, wherein an insulating jacket (10) covers an exterior side of the closed chamber (1), and the insulating jacket (10) is provided with a temperature control system.

3. The evaporation closed chamber for detecting a hazardous substance according to claim 1, wherein a protective cover (11) covers an outer side face of the gas compensation device (5), and the protective cover (11) covers an outer side face of the pressure plate (7).

4. The evaporation closed chamber for detecting a hazardous substance according to claim 1, wherein a closed chamber door (12) is arranged on the closed chamber (1), and a temperature and/or humidity control device (13) is arranged at the interior/exterior of the closed chamber (1).

5. The evaporation closed chamber for detecting a hazardous substance according to claim 1, wherein a stirrer (14) is arranged in the closed chamber (1).

6. The evaporation closed chamber for detecting a hazardous substance according to claim 1, wherein an anti-adsorption coating configured for preventing adsorption of the hazardous substance is arranged on an inner wall of the closed chamber (1).

7. The evaporation closed chamber for detecting a hazardous substance according to claim 1, wherein an exhaust valve (15) is arranged on the exhaust pipe (3).

8. The evaporation closed chamber for detecting a hazardous substance according to claim 1, wherein the closed chamber (1) is connected with an internal purification device (19), the internal purification device (19) comprises a purification loop (20), an air inlet valve (21), an air outlet valve (22), a purification filter (23) and a second fan (24), and two ends of the purification loop (20) are respectively connected with the closed chamber (1).

9. The evaporation closed chamber for detecting a hazardous substance according to claim 1, wherein an intake valve (25) and an intake flow meter (26) are arranged at the exterior of the closed chamber (1).

10. The evaporation closed chamber for detecting a hazardous substance according to claim 1, wherein the elastic film (9) is a fluoride elastic film.

* * * * *